US007087628B2

(12) United States Patent
Sui et al.

(10) Patent No.: US 7,087,628 B2
(45) Date of Patent: Aug. 8, 2006

(54) N-HETEROCYCLYL HYDRAZIDES AS NEUROTROPHIC AGENTS

(75) Inventors: Zhihua Sui, Flemington, NJ (US); Mark Macielag, Branchburg, NJ (US); James Lanter, Hillsborough, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 196 days.

(21) Appl. No.: 10/264,997

(22) Filed: Oct. 4, 2002

(65) Prior Publication Data

US 2003/0144262 A1 Jul. 31, 2003

Related U.S. Application Data

(60) Provisional application No. 60/327,019, filed on Oct. 4, 2001.

(51) Int. Cl.
*A61K 31/4439* (2006.01)
*C07D 401/12* (2006.01)

(52) U.S. Cl. .................................... 514/343; 546/279.1

(58) Field of Classification Search ............. 546/279.1; 514/353, 343
See application file for complete search history.

(56) References Cited

U.S. PATENT DOCUMENTS 4,665,173 A * 5/1987 Klayman et al. ........... 540/597
4,694,004 A * 9/1987 Nakaguti et al. ........ 514/237.2
6,271,247 B1 * 8/2001 Monge Vega et al. ...... 514/356
6,555,542 B1 * 4/2003 O'Connor et al. ..... 514/253.09

FOREIGN PATENT DOCUMENTS

WO WO 01 04090 A 1/2001
WO WO 01 04091 A 1/2001

OTHER PUBLICATIONS

PCT International Search Report dated Dec. 17, 2002.

* cited by examiner

*Primary Examiner*—Kamal A. Saeed
*Assistant Examiner*—Rebecca Anderson

(57) ABSTRACT

This invention relates to a series of N-heterocyclyl hydrazides of Formula I,

I and pharmaceutical compositions containing them. The compounds of the invention have neurotrophic activity and are useful in the treatment and prevention of neuronal disorders such as Parkinson's disease, Alzheimer's disease, stroke, multiple sclerosis, amyotrophic lateral sclerosis diabetic neuropathy and Bell's palsy.

6 Claims, No Drawings

N-HETEROCYCLYL HYDRAZIDES AS NEUROTROPHIC AGENTS

This application claims priority from U.S. provisional application 60/327,019 filed Oct. 4, 2001 and entitled "N-heterocyclyl Hydrazides as Neurotrophic Agents" the contents of which are hereby incorporated by reference in their entirety.

FIELD OF THE INVENTION

This invention relates to certain novel N-heterocyclyl hydrazides having neurotrophic activity. These compounds, along with related compositions and methods, are useful in the treatment and prevention of neuronal disorders such as Parkinson's disease, Alzheimer's disease, stroke, multiple sclerosis, amyotrophic lateral sclerosis, diabetic neuropathy, and Bell's palsy.

BACKGROUND OF THE INVENTION

Neurodegenerative diseases constitute a major threat to public health throughout the world. One of the most serious of such diseases is Alzheimer's disease (AD), a major cause of dementia in aged humans and the fourth most common medical cause of death in the United States. In the U.S., it is estimated that AD afflicts two to three million individuals overall, and more than 5% of the population over the age of 65. Although the exact etiology of AD remains to be defined, the disease is characterized by the presence of a large number of amyloid plaques and neurofibrillary tangles in regions of the brain involved in cognitive function, and degeneration of cholinergic neurons that ascend from the basal forebrain to cortical and hippocampal areas. Currently, there are no effective therapies for AD (Brinton, R. D. and Yamazaki, R. S., *Pharm. Res.,* 1998, 15:386–98).

Similar to AD, Parkinson's Disease (PD) is a progressive degenerative disease of the central nervous system (CNS). The lifetime incidence of the disease is approximately 2% in the general population. In PD, degeneration of the dopaminergic neurons of the substantia nigra leads to a decrease in dopamine levels in the region of the brain controlling voluntary movement, the corpus striatum. Therefore, standard treatments have focused on the administration of agents, like L-dopa and bromocriptine, which replenish dopamine levels in the affected areas of the brain. Dopaminergic regimens lose their efficacy, however, as nerve cells continue to die and the disease progresses. At the same time the involuntary tremors seen in the early stages of PD advance to periods of difficult movement and, ultimately, to immobility. Therefore, alternative therapies are actively being sought (Pahwa, R. and Koller, W. C., *Drugs Today,* 1998, 34:95–105).

Neurodegenerative diseases of the somatosensory nervous system also constitute a class of debilitating and potentially lethal conditions. Amyotrophic lateral sclerosis (ALS) is a fatal disease characterized by progressive degeneration of the upper and lower motor neurons. Although the precise etiology of ALS is unknown, popular theories suggest that excitotoxicity and/or oxidative stress are contributing factors. Riluzole is the first drug approved and marketed for ALS. It possesses antiexcitotoxic properties and has been shown to increase the rate of survival of ALS patients. However, the drug is not a cure, and clinical trials of alternative agents are currently underway (Louvel, E., Hugon, J. and Doble, A., *Trends Pharmacol. Sci.,* 1997, 18:196–203).

Peripheral neuropathies are secondary to a number of metabolic and vascular conditions. In particular, approximately 30% of patients with diabetes mellitus suffer from some form of peripheral neuropathy that may affect the small myelinated fibers, causing loss of pain and temperature sensation, or the large fibers, causing motor or somatosensory defects. Pharmacotherapeutic intervention tends to be symptomatic, and the best approach to treatment and prevention remains the maintenance of normal blood glucose levels through diet and insulin administration (Biessels, G. J. and Van Dam, P. S., *Neurosci. Res. Commun.,* 1997, 20:1–10).

A considerable body of evidence now suggests that deficiencies in the levels of certain proteinaceous growth factors, or neurotrophic factors, may play key pathoetiological roles in both peripheral and central neurodegenerative diseases (Tomlinson et al., *Diabetes,* 1997, 46(suppl. 2):S43-S-49; Hamilton, G. S., *Chem. Ind.*, (*London*) 1998, 4:127–132; Louvel et al., *Trends Pharmacol. Sci.,* 1997, 18:196–203; Ebadi et al., *Neurochem. Int.,* 1997, 30:347–374).

These neurotrophic factors can be divided into two structural classes: 1) the neurotrophins, including nerve growth factor (NGF); glial cell-derived neurotrophic growth factor (GDNF); brain-derived neurotrophic factor (BDNF); neurotrophin 3 (NT-3); neurotrophin 4/5 (NT-4/5); neurotrophin 2 (NT-2); and ciliary neurotrophic factor (CNTF) which is related to the cytokine family of molecules. All neurotrophic factors promote neurite outgrowth, induce differentiation, and suppress programmed cell death or apoptosis in specific subpopulations of peripheral and central neurons. For example, NGF exerts trophic effects on sympathetic and sensory neurons of the dorsal root ganglion and cholinergic neurons of medial septum in the CNS, suggesting potential therapeutic utility in AD. CNTF has trophic actions on a broad cross-section of neurons, including parasympathetic, sensory, sympathetic, motor, cerebellar, hippocampal, and septal neurons. Of particular interest is the fact that CNTF partially prevents the atrophy of skeletal muscle following the formation of nerve lesions but has no effect on innervated muscle, indicating that CNTF is primarily operative in the pathological state. As a result, CNTF is currently being evaluated for its effects in musculoskeletal diseases like ALS.

The clinical utility of proteinaceous neurotrophic agents is severely hampered by their limited bioavailability, especially in the CNS. This necessitates the administration of these agents directly into the brain to induce a therapeutic effect. Direct introduction of agents into the brain is a relatively hazardous and cumbersome route of administration.

Protein based compounds currently in clinical use as neurotrophic agents cannot be administered orally and otherwise show poor bioavailability except when administered intracerebroventricularly, "ICV," for a CNS indication or intravenously for peripheral nerve dysfunctions such as diabetic neuropathy or Bell's palsy. Accordingly, there is a clear need for bioavailable small molecule mimetics of neurotrophic factors that are orally bioavailable and can readily penetrate the blood-brain barrier.

Great efforts have been made to identify small molecules having neurotrophic activity, but all such compounds reported so far are structurally dissimilar to N-heterocyclyl hydrazides.

SUMMARY OF THE INVENTION

This invention provides novel N-heterocyclyl hydrazides having surprising neurotrophic activity. Demonstrated to have these biological activities by in vitro and in vivo assays described hereinafter are the compounds of the present invention as shown in Formula I:

I

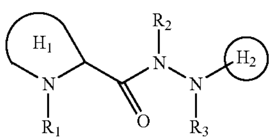

or a pharmaceutically acceptable salt thereof, wherein $H_1$ is selected from the group consisting of a 4-membered nitrogen-containing heterocyclyl having 3 carbon ring atoms, a 5-membered nitrogen-containing heterocyclyl having 0 or 1 additional heteroatom ring member selected from O, S, and N, and a 6- or 7-membered nitrogen-containing heterocyclyl having 0, 1, or 2 additional heteroatom ring members selected from O, S, and N;

$H_2$ is a 5- or 6-membered heteroaryl;

$R_1$ is selected from urea, $C_1$–$C_{10}$ alkyl, aryl, heteroaryl, heterocyclyl, —C(O)R, —C(O)—C(O)R, —$SO_2$R, and —P(O)(OR')(OR"), wherein R, R', and R" are independently selected from alkyl, aryl, heteroaryl, and heterocyclyl; and $R_2$ and $R_3$ are independently hydrogen or $C_1$–$C_{10}$ alkyl.

This invention also provides a pharmaceutical composition comprising the instant compound and a pharmaceutically acceptable carrier, as well as related synthetic methods.

This invention further provides a method of treating a subject suffering from a condition characterized by neuronal damage caused by disease or trauma, which method comprises administering to the subject a therapeutically effective dose of the instant pharmaceutical composition.

This invention still further provides a method of inhibiting in a subject the onset of a condition characterized by neuronal damage caused by disease or trauma, which method comprises administering to the subject a therapeutically effective dose of the instant pharmaceutical composition.

DETAILED DESCRIPTION OF THE INVENTION

This invention provides novel triazepine compounds having surprising neurotrophic activity. These compounds, along with related pharmaceutical compositions and methods, are useful in the treatment and prevention of neuronal disorders including, for example, Parkinson's disease, Alzheimer's disease, stroke, multiple sclerosis, amyotrophic lateral sclerosis, diabetic neuropathy or Bell's palsy. They are also useful in the treatment of disorders caused by trauma to the brain, spinal cord or peripheral nerves.

Specifically, this invention provides a compound of Formula I,

I

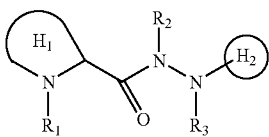

or a pharmaceutically acceptable salt thereof, wherein $H_1$ is selected from the group consisting of a 4-membered nitrogen-containing heterocyclyl having 3 carbon ring atoms, a 5-membered nitrogen-containing heterocyclyl having 0 or 1 additional heteroatom ring member selected from O, S, and N, and a 6- or 7-membered nitrogen-containing heterocyclyl having 0, 1, or 2 additional heteroatom ring members selected from O, S, and N;

$H_2$ is a 5- or 6-membered heteroaryl;

$R_1$ is selected from urea, $C_1$–$C_{10}$ alkyl, aryl, heteroaryl, heterocyclyl, —C(O)R, —C(O)—C(O)R, —$SO_2$R, and —P(O)(OR')(OR"), wherein R, R', and R" are independently selected from alkyl, aryl, heteroaryl, and heterocyclyl; and $R_2$ and $R_3$ are independently hydrogen or $C_1$–$C_{10}$ alkyl.

More specifically, this invention provides a compound of Formula Ia,

Ia

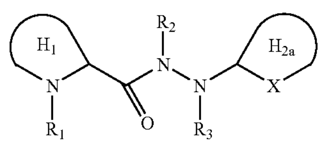

wherein $H_{2a}$ is a 5- or 6-membered heteroaryl wherein X is a heteroatom selected from O, S, and N, and $R_1$, $R_2$, $R_3$, and $H_1$ are as described above.

More specifically, this invention provides a compound of Formula Ib,

Ib

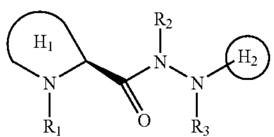

wherein $R_1$, $R_2$, $R_3$, $H_1$, and $H_2$ are as described above.

In one embodiment of the instant compound, $R_1$ is selected from the group consisting of —C(O)R, —C(O)—C(O)R, and —$SO_2$R wherein R is selected from the group consisting of aryl, heteroaryl, cycloalkyl, and $C_4$–$C_{10}$ straight or branched alkyl. In another embodiment, $H_2$ is a pyridine. In yet another embodiment, $R_2$ and $R_3$ are independently $C_1$–$C_5$ alkyl. In still another embodiment, $R_1$ is selected from $C_4$–$C_{10}$ alkyl, aryl, heteroaryl, and heterocyclyl.

Unless specified otherwise, the term "alkyl" refers to a straight, branched or cyclic substituent consisting solely of carbon and H with or without unsaturation, optionally substituted with one or more independent groups including, but not limited to, halogen, OH, amino, alkoxy, aryl, substituted aryl, heteroaryl, substituted heteroaryl, heterocyclyl, and substituted heterocyclyl. The term "alkoxy" refers to O-alkyl where alkyl is as defined supra. The term "halo" or "halogen" means fluoro, chloro, bromo or iodo.

The term "aryl" or "aromatic ring" refers to a 5- to 6-membered ring containing a 6-electron delocalized conjugated pi bonding system such as phenyl, furanyl, and pyrrolyl. The term "aryl" or "aromatic ring" includes mono and fused aromatic rings such as phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. The symbol "Ph" refers to phenyl.

The term "heteroaryl" as used herein represents a stable five or six-membered monocyclic or bicyclic aromatic ring system which consists of carbon atoms and from one to three heteroatoms selected from N, O and S. The heteroaryl group may be attached at any heteroatom or carbon atom, which results in the creation of a stable structure. Examples of heteroaryl groups include, but are not limited to pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl.

Unless specified otherwise, aryl or heteroaryl may be substituted by one to three independent groups such as halogen, aryl, heteroaryl, OH, CN, mercapto, nitro, $C_{1-10}$-alkyl, halo-$C_{1-10}$-alkyl, $CF_3$, $C_{1-10}$-alkoxy, $C_{1-10}$-alkylthio, amino, $C_{1-10}$-alkyl-amino, di($C_1$–$C_8$-alkyl-)amino, arylamino, nitro, formyl, carboxyl, alkoxycarbonyl, $C_{1-10}$-alkyl-CO—O—, $C_{1-10}$-alkyl-CO—NH—, and carboxamide. The substituted heteroaryl may also be substituted with a substituted aryl or a second substituted heteroaryl to give, for example, a 2-phenylpyrimidine or a 2-(pyrid-4-yl)pyrimidine, and the like. Unless specified otherwise, the terms "substituted aryl" and "substituted heteroaryl" include aryl and heteroaryl that are fused with one or more 3- to 8-membered cycloalkyl or 5- to 7-membered ring systems selected from the group consisting of aryl, heteroaryl, and heterocyclyl.

"Heterocyclyl" or "heterocycle" is a 3- to 8-member saturated or partially saturated, single or fused ring system which consists of carbon atoms and from one to four heteroatoms selected from N, O and S. Unless specified otherwise, the heterocyclyl group may be attached at any heteroatom or carbon atom which results in the creation of a stable structure. Examples of heterocyclyl groups include, but are not limited to, pyridine, pyrimidine, oxazoline, pyrrole, imidazole, morpholine, furan, indole, benzofuran, pyrazole, pyrrolidine, piperidine, and benzimidazole. The "heterocyclyl" or "heterocycle" may be substituted with one or more independent groups including, but not limited to, H, halogen, oxo, OH, $C_1$–$C_{10}$ alkyl, $CF_3$, amino, and alkoxy. Unless specified otherwise, substituted heterocyclyl includes heteroaryl fused with one or more 3- to 8-membered cycloalkyl or 5- to 7-membered ring systems selected from aryl, heteroaryl, and heterocyclyl.

The instant compounds can be isolated and used as free bases. They can also be isolated and used as pharmaceutically acceptable salts. The phrase "pharmaceutically acceptable salt" denotes salts of the free base which possess the desired pharmacological activity of the free base and which are neither biologically nor otherwise undesirable. These salts may be derived from inorganic or organic acids. Examples of inorganic acids are hydrochloric acid, hydrobromic acid, hydroiodic acid, perchloric acid, nitric acid, sulfuric acid and phosphoric acid. Examples of organic acids are acetic acid, propionic acid, glycolic acid, lactic acid, pyruvic acid, malonic acid, succinic acid, malic acid, maleic acid, maleic acid, fumaric acid, tartaric acid, citric acid, benzoic acid, cinnamic acid, mandelic acid, oxalic acid, pamoic acid, saccharic acid, methanesulfonic acid, ethanesulfonic acid, p-toluenesulfonic acid, methyl sulfonic acid, salicyclic acid, hydroethanesulfonic acid, benzenesulfonic acid, 2-naphthalenesulfonic acid, p-toluenesulfonic acid, cyclohexanesulfamic acid and the like. Alternatively, "pharmaceutically acceptable salt" denotes salts of the free acid which possess the desired pharmacological activity of the free acid and which are neither biologically nor otherwise undesirable. These salts may be derived from a metal ion or an organic base, such as Li, Na, K, $NH_4$ and the like.

Where the compounds according to this invention have one or more stereogenic centers, it is to be understood that all possible optical isomers, antipodes, enantiomers, and diastereomers resulting from additional stereogenic centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids. Alternatively, the antipodes can be separated by chromatography in a Pirkle-type column.

Some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The following compounds are exemplary of the present invention:

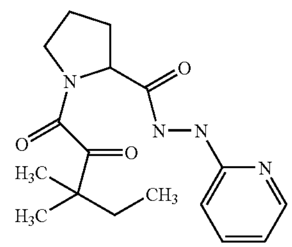

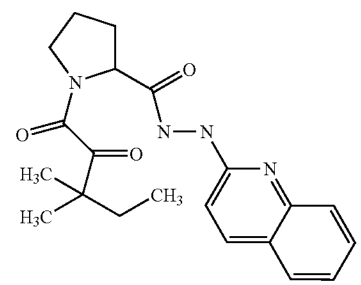

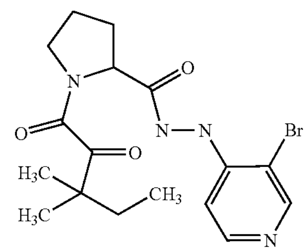

-continued

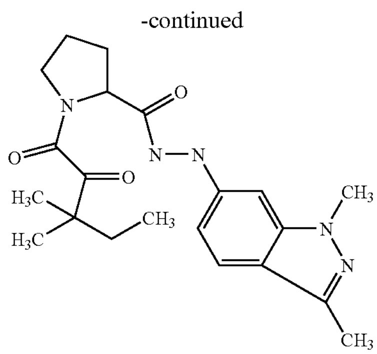

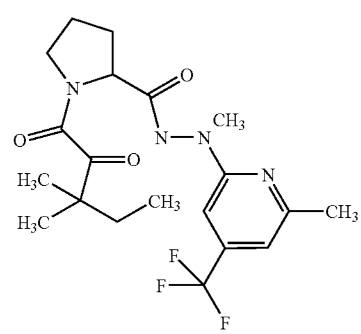

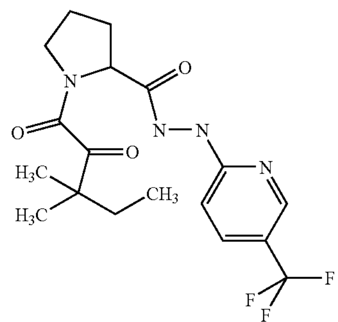

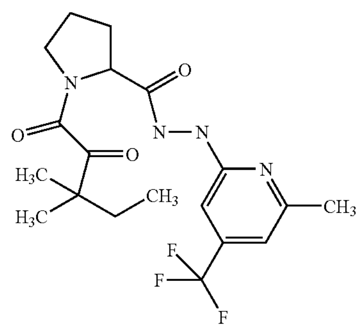

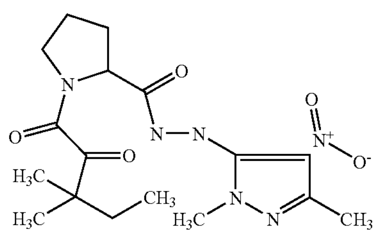

-continued

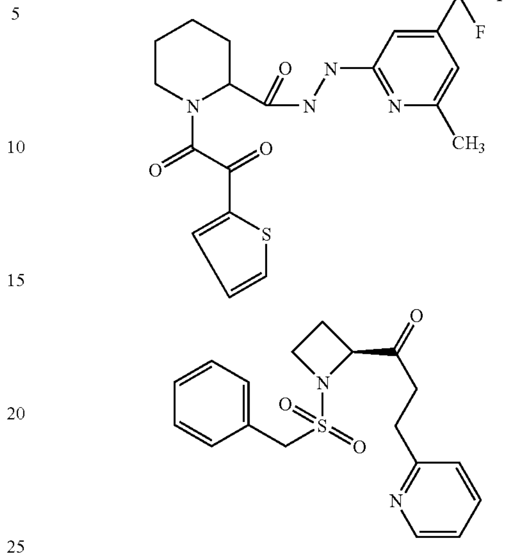

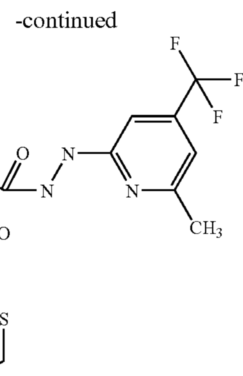

In one embodiment, the compound of the invention is selected from:

1-(3,3-dimethyl-2-oxo-pentanoyl)-pyrrolidine-2-carboxylic acid N'-pyridine-2-yl-hydrazide;

1-(2-oxo-2-thiophen-2-yl-acetyl)piperidine-2-carboxylic acid N'-(6-methyl-4-trifluoromethyl-pyridin-2-yl)-hydrazide; and 2-azetidinecarboxylic acid, 1-[(phenylmethyl)sulfonyl]-, 2-(2-pyridinyl)hydrazide, (2S)-.

This invention also provides a pharmaceutical composition comprising the instant compound and a pharmaceutically acceptable carrier.

Pharmaceutical compositions containing the compound of the present invention as the active ingredient in intimate admixture with a pharmaceutical carrier can be prepared according to conventional pharmaceutical techniques. The carrier may take a wide variety of forms depending on the form of preparation desired for administration, such as topical administration and systemic administration including, but not limited to, intravenous infusion, oral, nasal or parenteral. In preparing the compositions in oral dosage form, any of the usual pharmaceutical carriers may be employed, such as water, glycerol, glycols, oils, alcohols, flavoring agents, preservatives, coloring agents, syrup and the like in the case of oral liquid preparations (for example, suspensions, elixirs and solutions); or carriers such as starches, sugars, methyl cellulose, magnesium sterate, dicalcium phosphate, mannitol and the like in the case of oral solid preparations (for example, powders, capsules and tablets). All excipients may be mixed as needed with disintegrants, diluents, granulating agents, lubricants, binders and the like using conventional techniques known to those skilled in the art of preparing dosage forms.

The preferred route of administration is oral administration. Because of their ease in administration, tablets and capsules represent an advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

This invention also provides a method of stimulating neuronal growth comprising contacting neurons with an effective amount of the instant compound. The contacting step can be performed, for example, in vitro, ex vivo or in vivo.

The compounds of the present invention stimulate neuronal growth. Thus, this invention further provides a method of treating a subject suffering from a condition characterized by neuronal damage caused by disease or trauma, which method comprises administering to the subject a therapeutically effective dose of the instant pharmaceutical composition. As used herein, the term "subject" includes, without limitation, any animal or artificially modified animal. In the preferred embodiment, the subject is a human.

In one embodiment, the disorder treated is caused by disease, and is selected from the group consisting of Parkinson's disease, Alzheimer's disease, stroke, multiple sclerosis, amyotrophic lateral sclerosis, peripheral neuropathy and Bell's palsy. In another embodiment, the disorder treated is caused by trauma to the brain, spinal cord or peripheral nerves.

This invention still further provides a method of inhibiting in a subject the onset of a condition characterized by neuronal damage caused by disease or trauma, which method comprises administering to the subject a prophylactically effective dose of the instant pharmaceutical composition.

In one embodiment, the condition is selected from the group consisting of Parkinson's disease, Alzheimer's disease, stroke, multiple sclerosis, amyotrophic lateral sclerosis, peripheral neuropathy and Bell's palsy. In the preferred embodiment, the condition is Alzheimer's disease.

pharmaceutical composition. The effective dose for administering the pharmaceutical composition to a human, for example, can be determined mathematically from the results of animal studies.

In one embodiment, oral doses of the instant compounds range from about 0.01 to about 200 mg/kg, daily. In another embodiment, oral doses range from about 0.1 to about 50 mg/kg daily, and in a further embodiment, from about 1 to about 30 mg/kg daily. Infusion doses can range, for example, from about 1.0 to $1.0\times10^4$ μg/kg/min of instant compound, admixed with a pharmaceutical carrier over a period ranging from several minutes to several days. For topical administration, the instant compound can be mixed with a pharmaceutical carrier at a concentration of, for example, about 0.1 to about 10% of drug to vehicle.

Finally, this invention provides processes for preparing the instant compounds. These compounds can be prepared as shown below from readily available starting materials and/or intermediates following processes well known in the art.

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

EXPERIMENTAL DETAILS

A. Schemes and Syntheses

The synthesis of the claimed compounds is summarized in Scheme I wherein $H_1$, $H_2$, $R_1$, $R_2$, $R_3$, R, R', and R" are as described hereinabove.

Scheme I

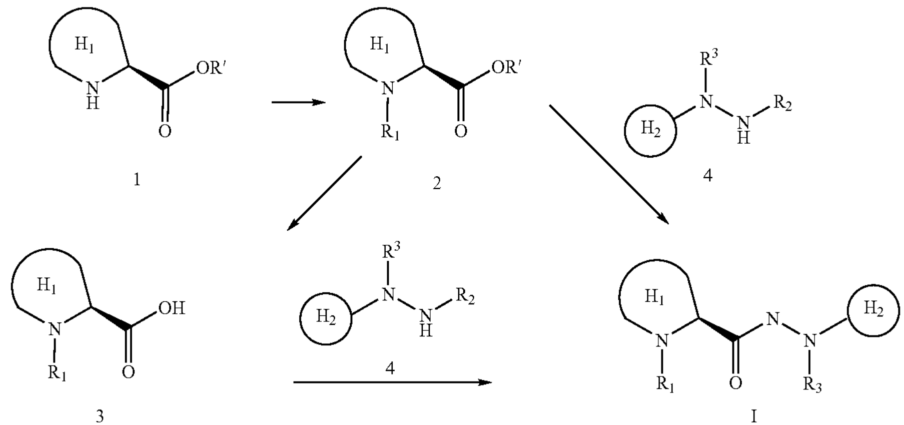

As used herein, "treating" a disorder means eliminating, reducing, limiting, or otherwise ameliorating the cause and/or effects thereof. "Inhibiting" the onset of a disorder means preventing, delaying or reducing the likelihood of such onset. Likewise, "therapeutically effective" and "prophylactically effective" doses are doses that permit the treatment and inhibition, respectively, of a disorder.

Methods are known in the art for determining therapeutically and prophylactically effective doses for the instant When $R_1$, is urea, compound 1 is reacted with an appropriately substituted isocyanate in an organic solvent, preferably DCM (dichloromethane), THF (tetrahydrofuran), or DMF (N,N-dimethylformamide), at a temperature preferably between −78–120° C. to give compound 2. When $R_1$ is alkyl or heterocyclyl, compound 1 is reacted with an appropriate halide, tosylate, mesylate or the like in an organic solvent such as DMF, DMSO (dimethyl sulfoxide), or acetone in the presence of a base such as TEA (triethylamine), DIEA (diisopropylethylamine), and $K_2CO_3$ at a temperature preferably between 10–150° C. When $R_1$ is aryl or heteroaryl, compound 1 is reacted with an appropriate halide, tosylate, mesylate or the like in the presence of an organometalic catalyst such as $Pd(Ac)_2$ and $Pd_2dba_3$ (dba: dibenzylideneacetone), and a base such as TEA, DIEA, and $K_2CO_3$ in an organic solvent such as THF, DMF, and DCM at a temperature preferably between 0–150° C. When $R_1$ is pyridine, pyrimidine, or other electron deficient heterocycles, the reaction can be conducted in the absence of the organometalic catalyst. When $R_1$ is —C(O)R, —C(O)—C(O)R, compound 1 is reacted with an appropriate carboxylic acid in the presence of a coupling reagent such as DCC (dicyclohexylcarbodiimide) and PyBrop (Bromo-tris-pyrrolidino-phosphonium hexafluorophosphate) in an organic solvent such as DCM, THF, and DMF at a temperature preferably between 0–80° C. Compound 1 can react with the acid halide of —C(O)R, —C(O)—C(O)R, —$SO_2$R, and —P(O)(OR')(OR") in the presence of a base such as TEA, DIEA, and $K_2CO_3$ in an organic solvent such as DCM, THF, and DMF to give 2.

Compound 2 can react with compound 4 in an organic solvent such as ethanol, DMF, DMSO, and toluene at a temperature preferably between 50–150° C. to give the corresponding compound of formula I. Alternatively, compound 2 can be hydrolyzed with a base such as LiOH and NaOH to give compound 3. Compound 3 can then react with 4 in the presence of a coupling reagent such as DCC and PyBrop in an organic solvent such as THF, DMF, and dioxane to give the corresponding compound of formula I.

The examples below describe in greater particularity the chemical synthesis of representative compounds of the present invention. The remaining compounds disclosed herein can be prepared similarly in accordance with one or more of these methods. No attempt has been made to optimize the yields obtained in these reactions, and it would be clear to one skilled in the art that variations in reaction times, temperatures, solvents, and/or reagents could increase such yields.

EXAMPLE 1

Compound (1)

1-(3,3-Dimethyl-2-oxo-pentanoyl)-pyrrolidine-2-carboxylic acid N'-pyridine-2-yl-hydrazide A mixture of (2S)-1-(1,2-dioxo-3,3-dimethylpentyl)-2-pyrrolidine-carboxylic acid (482 mg, 2 mmol), prepared from L-proline methyl ester according to the procedure described in WO 96/40633, 2-hydrazinopyridine (364 mg, 2 mmol), PyBrop (932 mg, 2 mmol), DMAP (4-dimethyaminopyridine, 122 mg) and DIEA (4 mL) in THF (dry, 50 mL) was stirred at room temperature for 24 h. Water and ethyl acetate were added. The organic phase was washed with ammonium chloride solution, followed by brine, and dried with $MgSO_4$. Column chromatography (silica gel, ethyl acetate:methanol=10:0.5) gave a colorless oil; 490 mg (74%); MS (m/z) 333 (M+1); $^1$H NMR ($d_6$-DMSO) δ0.85 (t, J=8 Hz, 3 H), 1.21 (s, 3 H), 1.23 (s, 3 H), 1.7 (m, 2 H), 1.90 (m, 1 H), 2.10 (m, 2 H), 2.35 (m, 1 H), 3.49 (t, J=8 Hz, 2 H), 4.62 (m, 1 H), 6.76 (m, 2 H), 7.51 (t, J=6 Hz, 1 H), 8.14 (d, J=6 Hz, 1 H).

Compounds (2)–(8) were synthesized in the manners similar to the above example.

EXAMPLE 2

Compound (9)

1-(2-Oxo-2-thiophen-2-yl-acetyl)piperidine-2-carboxylic acid N'-(6-methyl-4-trifluoromethyl-pyridin-2-yl)-hydrazide Intermediate 1: Methyl 1-(1,2-Dioxo-2-methoxy)-2-piperidinecarboxylate A solution of methyl pipecolinate hydrochloride (7.2 g, 40 mmol) in dry DCM (100 mL) and TEA (8.3 g) was cooled to 0° C. The slurry was stirred for 1 h. Methyl oxalyl chloride was added. The mixture was stirred at 0° C. for 2 h. Water was added, and the organic phase was washed with a $NaHCO_3$ solution, dried with $MaSO_4$. Evaporation of the solvent and drying in vacuum gave a reddish oil; 9.1 g (99%); MS (m/z) 252 (M+Na).

Intermediate 2: Methyl 1-[1,2-Dioxo-2-(thien-2-yl)ethyl)-2-piperidinecarboxylate To a solution of Intermediate 1 (2.29 g, 10 mmol) in THF at −78° C., a solution of thienyllithium (1.0 M, 13 ml, 13 mmol) was added slowly. The mixture was stirred at the same temperature for 4 h, quenched with ammonium chloride solution, extracted with ethyl acetate, and dried with $MgSO_4$. After evaporation of the solvent, a reddish oil was obtained; 2.51 g (89%); MS (m/z) 304 (M+Na).

Intermediate 3: 1-[1,2-Dioxo-2-(thien-2-yl)ethyl)-2-piperidinecarboxylic acid

Intermediate 2 (2.45 g, 8.72 mmol) was dissolved in MeOH (50 mL). LiOH solution (1 N, 13 mL) was added at 0° C., and the mixture was stirred at the same temperature for 2 h and at room temperature for 16 h. The reaction mixture was acidified with 1 N HCl, and extracted with ethyl acetate. The organic phase was washed with brine and dried with $MgSO_4$. After evaporation of the solvent and drying under vacuum, a yellow solid was obtained, and was used for the next step without purification.

Compound (9): 1-(2-Oxo-2-thiophen-2-yl-acetyl)piperidine-2-carboxylic acid N'-(6-methyl-4-trifluoromethyl-pyridin-2-yl)-hydrazide From Intermediate 3 (267 mg, 1 mmol), 2-hydrazino-6-methyl-4-trifluoromethylpyridine (191 mg, 1 mmol), PyBrop (466 mg, 1 mmol), DMAP (122 mg) and DIEA (2 mL) in THF (30 mL), using the same procedure for Compound 1, the title compound was obtained as a white solid; 110 mg (25%). MS (m/z) 441 (M+1).

EXAMPLE 3

Compound (10)

2-Azetidinecarboxylic acid, 1-[(phenylmethyl)sulfonyl]-, 2-(2-pyridinyl)hydrazide, (2S)-

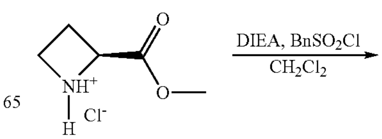

-continued

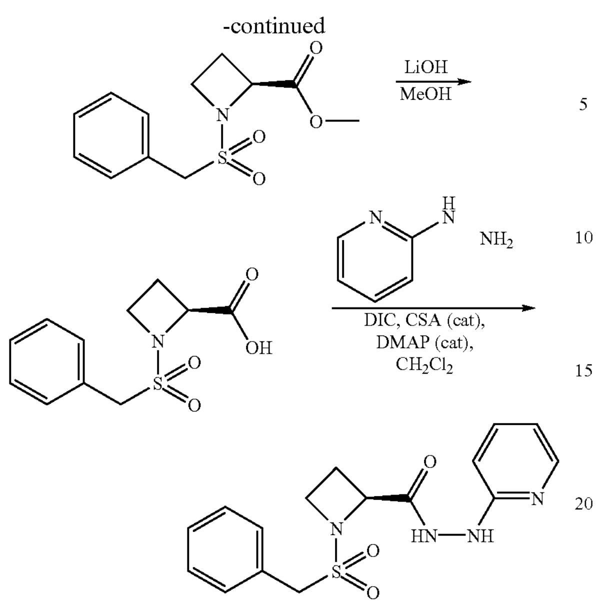

1-Phenylmethanesulfonyl-azetidine-2-carboxylic acid methyl ester:

Azetidine-2-carboxylic acid (560 mg, 5.5 mmoles) was suspended in methanol (25 mL) and cooled to −5° C. under an argon atmosphere. Thionyl chloride was added dropwise and the mixture was allowed to warm to room temperature over a 3 hour period. After concentration in vacuo, the residue was dissolved in dry dichloromethane (25 mL) and treated sequentially with benxzyl sulfonyl chloride (1.17 g, 6.14 mmoles) and diisopropylethylamine (2.15 mL, 12.3 mmoles). After stirring overnight, the mixture was concentrated and purified by flash chromatography on silica gel to afford 1.13 g (76%) of the product as a colorless oil. $^1$H NMR ($CDCl_3$) δ2.29–2.51 (m, 2H); 3.21–3.29 (m, 1H); 3.81 (s, 3H); 4.02 (q, 1H, J=8.6); 4.32 (d, 1H, J=14.6); 4.46 (d, 1 H, J=14.6); 4.86 (dd, 1H, 9.4, 8.6); 7.34–7.43 (m, 3H); 7.46–7.54 (m, 2H).

1-Phenylmethanesulfonyl-azetidine-2-carboxylic acid:

1-Phenylmethanesulfonyl-azetidine-2-carboxylic acid methyl ester (1.13 g, 4.19 mmoles) was dissolved in methanol (20 mL) and cooled to 0° C. Treatment of this solution with aqueous lithium hydroxide (7.75 mL, 1 M) was followed by warming to ambient temperature over a 3 hour period. Most of the methanol was removed in vacuo and the pH was adjusted to 1 by treatment with 1 M HCl. The product was extracted into ethyl acetate, dried over anhydrous sodium sulfate and concentrated to afford 886 g (83%) of the product as a white solid. $^1$H NMR ($CDCl_3$) δ2.37–2.57 (m, 2H); 3.21–3.31 (m, 1H); 3.81 (s, 3H); 4.01 (q, 1H, J=8.6); 4.33 (d, 1H, J=13.7); 4.44 (d, 1 H, J=13.7); 4.98 (dd, 1H, 9.4, 8.6); 7.34–7.53 (series of m, 5H).

1-Phenylmethanesulfonyl-azetidine-2-carboxylic acid N'-pyridin-2-yl-hydrazide:

1-Phenylmethanesulfonyl-azetidine-2-carboxylic acid (142 mg, 0.56 mmoles) was dissolved in dry dichloromethane (10 mL) and treated with pyridin-2-yl-hydrazine (60 mg, 0.55 mmoles), diisopropylcarbodiimide (0.09 mL, 0.57 mmoles), camphorsulfonic acid (44 mg, 0.19 mmoles), and DMAP (23 mg, 0.19 mmoles). After stirring overnight at room temperature, the solution was concentrated and purified by flash chromatography on silica gel to afford 16 mg (8%) of the product as a yellow foam. $^1$H NMR ($CDCl_3$) δ2.36–2.47 (m, 2H); 3.43–3.52 (m, 1H); 3.93 (q, 1H, J=10.3); 4.33 (q, 2H, J=13.7); 4.83 (t, 1 H, J=8.6); 6.53 (d, 1H, J=8.6); 6.70–6.77 (m, 1H); 6.85 (br s, 1H); 7.26–7.54 (series of m, 6H); 8.11 (d, 1H, J=6.0); 8.36 (br s, 1 H).

B. Assays

Results from Example 6 are shown in Table 1. Examples 5 and 6 detail the methods used for preparation of the cell cultures used in Example 7.

EXAMPLE 5

Dorsal Root Ganglion (DRG) Culture

DRG were dissected from newborn or 1-day-old CD rats and placed into PBS on ice. After rinsing twice with sterile plating medium, DRG were transferred to empty wells of a 6-well plate coated with polyornithine/laminin (Becton Dickinson Labware) using #7 curved forceps. Three ml/well of plating medium was then added very gently, so as not to disturb the DRG. Plating medium is Leibovitz's L-15 medium (Gibco), plus 0.6% glucose, 33 mM KCl, 10% FCS, 10 mM Hepes and penicillin/streptomycin/glutamine. After overnight incubation at about 37° C. in 5% $CO_2$, this medium was replaced with 3 mL/well of assay medium [Leibovitz's L-15 medium plus 0.6% glucose, 1% FCS, 1% N-2 supplement (Gibco), 10 μM ara-C, 10 mM Hepes, and penicillin/streptomycin/glutamine] containing either vehicle (DMSO, 1/200,000), positive control (2–4 ng/mL NGF) or test compound (50–250 nM). All media were prepared fresh daily. DRG were microscopically examined for neurite outgrowth on days 1–5. Under optimal conditions, vehicle treatment did not induce neurite outgrowth from DRG. An experiment was considered positive (+) if the instant compound induced neurites of ≧1 diameter of the DRG.

EXAMPLE 6

Primary Rat Hippocampal Cells

Hippocampal cells were dissected from the brains of embryonic day 18 rat pups and dissociated with trypsin (1 mg/mL) and trituration. Cells were seeded at 30,000 cells/well in 96-well plates filled with 100 μL MEM and 10% FBS. At 7 days in culture, cells were fixed with 4% paraformaldehyde and immuno-fluorescence was performed.

EXAMPLE 7

Human M17 Neuroblastoma Cells

M17 human neuroblastoma cells were cultured in 1:1 ratio of EMEM and Ham's F12 with 1×NEAA and 10% FBS. The culture media contained 1×PSN antibiotic and was exchanged every other day, and the cells were passed in log phase near confluence.

TABLE 1

In Vitro Neurotrophic Activity

| Compound No. | Structure | MS (M + 1)+ | Rat Hippocampal Cell Response |
|---|---|---|---|
| (1) | O, O, N, N, N, N, $H_3C$, $CH_3$, $H_3C$, O | 333 | 157 |
| (2) | O, O, N, N, N, N, $H_3C$, $CH_3$, $H_3C$, O | 383 | 107 |
| (3) | O, O, N, N, N, Br, $H_3C$, $CH_3$, $H_3C$, O, N | 410 | 106 |
| (4) | O, O, N, N, N, N, $CH_3$, N, N, $H_3C$, $CH_3$, $H_3C$, O, $H_3C$, $CH_3$ | 415 | 105 |
| (5) | O, O, N, N, N, O, $N^+$, $O^-$, $H_3C$, $CH_3$, N, C, $H_3C$, O, N, $CH_3$ | 395 | <100 |

TABLE 1-continued
| Compound No. | Structure | MS (M + 1)+ | Rat Hippocampal Cell Response |
|---|---|---|---|
| | | In Vitro Neurotrophic Activity | |
| (6) | 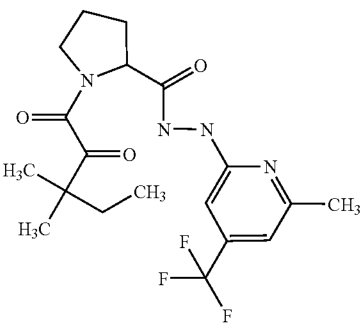 | 415 | <100 |
| (7) | 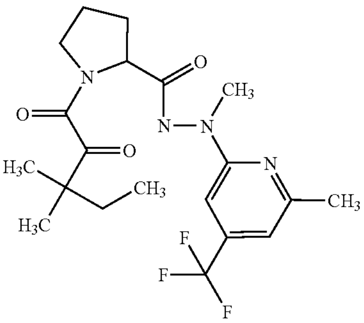 | 429 | <100 |
| (8) | 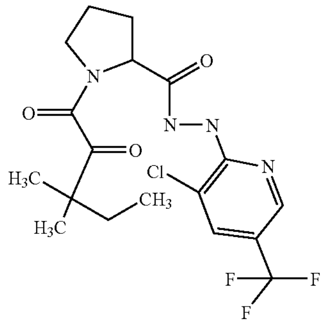 | 435 | 106 |
| (9) | 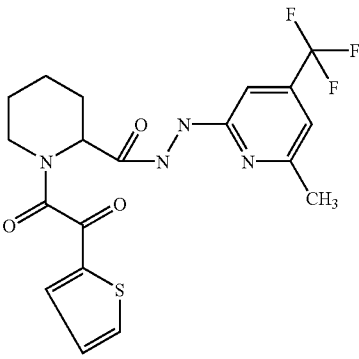 | 441 | 118 |

TABLE 1-continued

In Vitro Neurotrophic Activity

| Compound No. | Structure | MS (M + 1)+ | Rat Hippocampal Cell Response |
|---|---|---|---|
| (10) | Ch | 347 | 115 |

EXAMPLE 8

Neurite Outgrowth Assay

Cultures were incubated with normal horse serum (1:50; Vector Labs) for about 20 min, rinsed and then incubated with primary antibody, microtubule associated-protein 2 (anti-mouse MAP-2; 1:1000; Chemicon) for about 2 h at about RT. Following primary antibody, cultures were rinsed and incubated with fluorescein anti-mouse IgG (rat absorbed; 1:50; Vector Labs) for about 1 h. After fluorescein incubation, the cultures were rinsed and read in PBS on a fluorescent plate reader (excitation: 485 nm; emission: 530 nm). A compound was regarded as active if the neurite outgrowth response was greater than the mean DMSO-treated control response on the same plate. The response to test compound was reported as percent of DMSO-treated control. The signal-to-noise separation was consistent: the fluorescence from DMSO control wells is at least two-fold greater than blank wells.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula I,

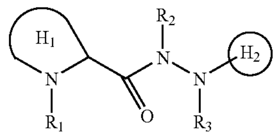

or a pharmaceutically acceptable salt thereof, wherein $H_1$ is a 5-membered heterocyclyl having one hetero atom which is nitrogen and no additional heteroatoms;

$H_2$ is a 6-membered heteroaryl having one hetero atom which is nitrogen and no additional heteroatoms; and $R_1$ is —C(O)—C(O)R, wherein R is selected from the group consisting of aryl, heteroaryl, cycloalkyl, and $C_4$–$C_{10}$ straight or branched alkyl and $R_2$ and $R_3$ are indecendentlv H or $C_1$–$C_{10}$ alkyl.

2. The compound of claim 1, wherein $H_2$ is attached at a β-carbon atom.

3. The compound of claim 1, wherein R is selected from the group consisting of cycloalkyl and $C_4$–$C_{10}$, straight or branched alkyl.

4. The compound of claim 3, wherein R is $C_4$–$C_{10}$ straight or branched alkyl.

5. The compound of claim 1 which is 1-(3,3-dimethyl-2-oxo-pentanoyl)-pyrrolidine-2-carboxylic acid N'-pyridine-2-yl-hydrazide.

6. A pharmaceutical composition comprising the compound of claim 1 and a pharmaceutically acceptable carrier.

* * * * *